United States Patent
Tsubokura et al.

(10) Patent No.: US 6,825,002 B2
(45) Date of Patent: Nov. 30, 2004

(54) PROCESS FOR PRODUCING CAROTENOID PIGMENTS

(75) Inventors: Akira Tsubokura, Kanagawa (JP); Haruyoshi Mizuta, Kanagawa (JP)

(73) Assignee: Nippon Mitsubishi Oil Corporation, Tokyo (JP)

( * ) Notice: Subject to any disclaimer, the term of this patent is extended or adjusted under 35 U.S.C. 154(b) by 194 days.

(21) Appl. No.: 10/049,228

(22) PCT Filed: Jun. 8, 2001

(86) PCT No.: PCT/JP01/04874

§ 371 (c)(1), (2), (4) Date: Feb. 11, 2002

(87) PCT Pub. No.: WO01/96591

PCT Pub. Date: Dec. 20, 2001

(65) Prior Publication Data

US 2003/0044886 A1 Mar. 6, 2003

(51) Int. Cl.$^7$ ............................................. C12P 23/00
(52) U.S. Cl. ........................ 435/67; 435/252.1; 435/244
(58) Field of Search .............................. 435/67, 252.1, 435/244

(56) References Cited

FOREIGN PATENT DOCUMENTS

| | | | |
|---|---|---|---|
| EP | 0 635 576 B1 | 8/2000 | |
| JP | 5-68585 A | 3/1993 | |
| JP | 8-9964 A | 1/1996 | |
| WO | WO 88/08025 A1 | 10/1988 | |

OTHER PUBLICATIONS

Yamane et al., Appl. and Environm. Microbiol., (1997) 63/11, 4471–4478.*

Anton Hartmann et al., "Effect of Carotenoid Overproduction on Oxygen Tolerance of Nitrogen Fixation in *Azospirillum brasilense* Sp7", Journal of General Microbiology, 1988, pp. 2449–2455, vol. 134.

* cited by examiner

*Primary Examiner*—Irene Marx
(74) *Attorney, Agent, or Firm*—Heller Ehrman White and McAuliffe LLP

(57) ABSTRACT

The present invention provides a method for changing production ratios of carotenoid compounds in a process of microbiological production of a plurality of carotenoid compounds. By controlling the concentration of dissolved oxygen in the culture during cultivation, production ratios of carotenoid compounds such as astaxanthin, adonixanthin, β-carotene, echinenone, canthaxanthin, zeaxanthin, β-cryptoxanthin, 3-hydroxyechinenone, asteroidenone and adonirubin, are changed.

8 Claims, No Drawings

PROCESS FOR PRODUCING CAROTENOID PIGMENTS

FIELD OF THE INVENTION

The present invention relates to a process of microbiological production of carotenoid compounds. More specifically, the present invention relates to a process of producing carotenoid compounds such as astaxanthin, adonixanthin, β-carotene, echinenone, canthaxanthin, zeaxanthin, β-cryptoxanthin, 3-hydroxyechinenone, asteroidenone and adonirubin.

BACKGROUND ART

Carotenoid compounds are natural pigments useful as feed additives, food additives, pharmaceuticals and the like. Especially, astaxanthin has a high industrial value as feed additives such as a color improver for bred fishes, e.g., salmon, trout or red sea bream, and as safe natural food additives. Likewise, adonixanthin is, if its industrial production process is established, promising as food additives, feed additives, pharmaceuticals, etc. Further, β-carotene has been used as feed additives, food additives, pharmaceuticals, etc.; canthaxanthin has been used as food additives, feed additives, cosmetics, etc.; and zeaxanthin has been used as food additives, feed additives, etc. Further, other carotenoid compounds such as echinenone, β-cryptoxanthin, 3-hydroxyechinenone, asteroidenone and adonirubin are also promising as feed additives, food additives, etc. As processes for producing these carotenoid compounds, such methods as chemical synthesis, production by microorganisms, and extraction from natural products are known. For astaxanthin, canthaxanthin and β-carotene, chemically synthesized products have already been commercialized.

Astaxanthin is contained in fishes such as red sea bream, salmon and trout, and in crustaceans such as shrimp, crab, crawfish and krill, and can be obtained through extraction from them. Examples of astaxanthin-producing microorganisms include red yeast *Phaffia rhodozyma;* a bacterium belonging to the genus Brevibacteriuin (Journal of General and Applied Microbiology, 15, 127, 1969); bacterial strain E-396 (FERM BP-4283) belonging to a novel genus (Japanese Unexamined Patent Publication Nos. 7-79796 and 8-9964; U.S. Pat. Nos. 5,607,839 and 5,858,761); bacterium *Agrobacterium aurantiacum* (Japanese Unexamined Patent Publication No. 7-184688); and green alga *Haematococcus pluvialis* (Phytochemistry, 20, 2561, 1981). As processes of chemical synthesis, conversion of β-carotene (Pure Appl. Chem. 57, 741, 1985) and synthesis from $C_{15}$ phosphonium salts (Helv. Chim. Acta. 64, 2436, 1981) are known.

It is known that Canthaxanthin is contained in certain species of mushrooms (Botanical Gazette, 112, 228–232, 1950), as well as fishes and crustaceans (Carotenoids of Marine Organisms, Journal of the Japanese Society of Fisheries Science, 1978). Examples of canthaxanthin-producing microorganisms include a microorganism belonging to the genus *Brevibacterium* (Applied and Environmental Microbiology, 55(10), 2505, 1989); a microorganism belonging to the genus *Rhodococcus* (Japanese Unexamined Patent Publication No. 2-138996); bacterial strain E-396 (FERM BP-4283) belonging to a novel genus (Japanese Unexamined Patent Publication Nos. 7-79796 and 8-9964; U.S. Pat. Nos. 5,607,839 and 5,858,761); and bacterium *Agrobacterium aurantiacum* (Biosci. Biotechnol. Biochem. 58, 1842, 1994). As processes of chemical synthesis, conversion of β-carotene (J. Amer. Chem. Soc., 78, 1427, 1956) and synthesis from a novel 3-oxo-$C_{15}$ phosphonium salt (Pure Appl. Chem., 51, 875, 1979) are known.

It is known that adonixanthin is contained in fishes such as goldfish and carp. However, its chemical synthesis is believed to be difficult, and no industrial process for production of adonixanthin has been known. Examples of adonixanthin-producing microorganisms include microorganisms belonging to the genera *Flavobacterium, Alcaligenes, Pseudomonas, Alteromonas, Hyphomonas* and *Caryophanon*, respectively (Japanese Unexamined Patent Publication No. 6-165684); bacterial strain E-396 (FERM BP-4283) belonging to a novel genus (Japanese Unexamined Patent Publication Nos. 7-79796 and 8-9964; U.S. Pat. Nos. 5,607,839 and 5,858,761); and bacterium *Agrobacterium aurantiacum* (Biosci. Biotechnol. Biochem. 58, 1842, 1994).

As processes for producing β-carotene, synthesis from β-ionone (Pure Appl. Chem. 63(1), 45, 1979) and extraction from green or yellow vegetables such as carrot, sweet potato or pumpkin (Natural Coloring Agent Handbook, Kohrin (1979), edited by Editorial Committee of Natural Coloring Agent Handbook) are known. Examples of β-carotene-producing microorganisms include algae belonging to genus *Dunaliella*, fungi belonging to genus *Blakeslea* (J. Appl. Bacteriol., 70, 181, 1991); bacterial strain E-396 (FERM BP-4283) belonging to a novel genus (Japanese Unexamined Patent Publication Nos. 7-79796 and 8-9964; U.S. Pat Nos. 5,607,839 and 5,858,761); and bacterium *Agrobacterium aurantiacum* (FEMS Microbiology Letters 128, 139, 1995).

Echinenone is extracted from natural products, e.g., starfishes such as crown of thorns, internal organs of fishes such as red sea bream, sea urchin, internal organs of crustaceans such as lobster, etc. Examples of echinenone-producing microorganisms include bacterial strain E-396 (FERM BP-4283) belonging to a novel genus (Japanese Unexamined Patent Publication Nos. 7-79796 and 8-9964; U.S. Pat Nos. 5,607,839 and 5,858,761) and bacterium *Agrobacterium aurantiacurn* (FEMS Microbiology Letters 128, 139, 1995).

As processes for producing zeaxanthin, chemical synthesis starting from an optically active hydroxy ketone obtained by asymmetric reduction of oxoisophorone (Pure Appl. Chem., 63(1), 45, 1991) and extraction from corn seeds (Biopigments, 1974, Asakura Shoten) are known. Examples of zeazanthin-producing microorganisms include a bacterium belonging to the genus *Flavobacterium* (Carotenoids, In Microbial Technology, 2nd Edition, Vol. 1, 529–544, Academic Press, New York); bacterial strain E-396 (FERM BP-4283) belonging to a novel genus (Japanese Unexamined Patent Publication Nos. 7-79796 and 8-9964; U.S. Pat. Nos. 5,607,839 and 5,858,761) and bacterium *Agrobacterium aurantiacum* (FEMS Microbiology Letters 128, 139, 1995).

However, the above-described production processes have various problems. For example, safety is not assured for the synthesized products; production by microorganisms is low in productivity; and extraction from natural products requires high cost. In the production of astaxanthin, for example, extraction from natural products such as krill or crawfish requires high cost since the content of astaxanthin is extremely small and yet the extraction is difficult. Red yeast *Phaffia rhodozyma* has a low growth rate, produces only small amounts of astaxanthin, and has a hard cell wall that makes the extraction of astaxanthin difficult. Thus, industrialization of astaxanthin production using this yeast is problematic. Green alga *Haemnatococcus pluvialis* also has many problems. Its growth rate is extremely low; this microorganism is easily contaminated; and extraction of astaxanthin therefrom is difficult. Thus, industrialization using this microorganism is problematic.

Bacterial strains E-396 (FERM BP-4283) and A-581-1 (FERM BP-4671) belonging to a novel genus (Japanese Unexamined Patent Publication Nos. 7-79796 and 8-9964; U.S. Pat. Nos. 5,607,839 and 5,858,761) have a number of advantages, e.g., high productivity, high growth rate, and easy extraction. However, since these microorganisms produce a plurality of carotenoid compounds such as astaxanthin, adonixanthin, β-carotene, echinenone, canthaxanthin, zeaxanthin, β-cryptoxanthin, 3-hydroxyechinenone, asteroidenone and adonirubin simultaneously, production ratios of these compounds vary from culture to culture, and it has been difficult to produce pigments at stable ratios. When the resultant pigment mixture is used in animal feeds, etc. as a color improver, the effect of color improvement varies rather widely. This has been an obstacle to commercial production of pigments using these microorganisms.

Thus, a process for stably producing carotenoid compounds at constant ratios has been desired.

The present invention has been made in view of such circumstances. It is an object of the present invention to control the production ratios of carotenoid compounds and to provide a process for stably producing carotenoid compounds at such controlled, specific ratios.

DISCLOSURE OF THE INVENTION

As a result of intensive and extensive researches toward the solution of the above-described problems, the present inventors have found that it is possible to control the production ratios of a plurality of carotenoid compounds and to produce the carotenoid compounds at such controlled, specific ratios, by appropriately controlling the concentration of dissolved oxygen in a culture during cultivation of a microorganism producing the carotenoid compounds. Thus, the present invention has been achieved.

The present specification includes the contents described in the specification and/or drawings of the Japanese Patent Application No. 2000-175124 based on which the present application claims priority.

BEST MODE FOR CARRYING OUT THE INVENTION

Hereinbelow, the present invention will be described in more detail.

In the process of the invention, carotenoid compounds-producing microorganisms are used. Examples of such microorganisms include carotenoid-producing bacteria, yeasts and fungi. One example of such bacteria is a bacterium in which the nucleotide sequence of a DNA corresponding to its 16S ribosomal RNA has 98% or more homology to the nucleotide sequence as shown in SEQ ID NO: 1. Specifically, bacterial strains E-396 (FERM BP-4283) and A-581-1 (FERM BP-4671); various mutant strains that can be obtained by mutating/improving these strains; and related species of these strains may be enumerated. The nucleotide sequence as shown in SEQ ID NO: 1 (DNA) corresponds to the 16S ribosomal RNA of E-396 strain, and the nucleotide sequence as shown in SEQ ID NO: 2 (DNA) corresponds to the 16S ribosomal RNA of A-581-1 strain.

Recently, classification of microorganisms based on the homology of nucleotide sequences of 16S ribosomal RNAs has become predominant as means for classifying microorganisms, because the conventional classification based on motility, auxotrophy, assimilation of saccharides, etc. has a problem that microorganisms may be identified erroneously when their characters have been changed by natural mutation or the like. The reliability of classification is remarkably improved when it is based on the homology of nucleotide sequences of 16S ribosomal RNAs since those nucleotide sequences are hereditarily very stable. The homology between the nucleotide sequences of the 16S ribosomal RNAs of E-396 strain and A-581-1 strain is 99.4%. This shows that these strains are closely related strains. Thus, these strains form a group of carotenoid-producing bacteria. E-396 strain and A-581-1 strain as well as those strains that produce effect under the culture conditions of the present invention are defined as a microorganism that has 98% or more homology to the nucleotide sequence of the 16S ribosomal RNA of E-396 strain as a mutant or related species of E-396 strain or A-581-1 strain.

Now, E-396 strain that is a specific example of the microorganism used in the present invention will be described below. This strain was newly isolated by the present inventors and deposited at the International Patent Organism Depository, National Institute of Advanced Industrial Science and Technology (AIST Tsukuba Central 6, 1-1, Higashi 1-chome, Tsukuba-shi, Ibaraki, Japan) on Apr. 27, 1993 as FERM BP-4283. Another specific example of the microorganism is A-581-1 strain (FERM BP-4671). This strain was newly isolated by the present inventors and deposited at the International Patent Organism Depository, National Institute of Advanced Industrial Science and Technology (AIST Tsukuba Central 6, 1-1, Higashi 1-chome, Tsukuba-shi, Ibaraki, Japan) on May 20, 1994 as FERM BP-4671.

The process of fermentation according to the invention is, for example, as described below. Briefly, a carotenoid-producing microorganism is cultured in a medium containing components that are necessary for the growth of the microorganism and generate carotenoid pigments.

The fermentation method may be conventional aerobic culture, such as aeration agitation culture, bubble column culture, or fluidized bed culture. Preferably, aeration agitation culture is used. For example, E-396 strain (FERM BP-4283) produces carotenoid compounds of β-carotene, echinenone, β-cryptoxanthin, 3-hydroxyechinenone, asteroidenone, canthaxanthin, zeaxanthin, adonixanthin, adonirubin and astaxanthin simultaneously.

The biosynthesis of astaxanthin is estimated as follows. The six-membered rings at both ends of β-carotene located upstream are modified by ketolase and hydroxylase, respectively, to finally produce astaxanthin. However, there has been observed a phenomenon that all of the carotenoid compounds are not converted into astaxanthin even if the fermentation period has been prolonged and that some part of these compounds remain unconverted until the end of the fermentation. Besides, the production ratios of these compounds vary by cultivation. For example, in one cultivation, the ratios of β-carotene, echinenone, canthaxanthin, adonirubin and 3-hydroxyechinenone that are believed to be located upstream in the biosynthesis pathway are high; in another cultivation, the production ratio of astaxanthin is high; and in still another cultivation, the production ratio of adonixanthin is high.

For the above-described reasons, the effect of color improvement varies rather widely when the resultant pigment mixture is used in animal feeds, etc. as a color improver. Thus, such pigment mixture cannot be sold as merchandise. This has been an obstacle to commercial production of such pigments. As a result of various researches toward the solution of this problem, the present inventors have found that a factor influencing the production ratios of pigments is the dissolved oxygen in the culture. It was found that, in agitation culture with a specific agitation/rotation speed, the concentration of dissolved oxygen in the culture is influenced by subtle differences in the oxygen consumption rate of the microorganism and, thus, the production ratios of pigments vary by culture lot. By controlling the concentration of dissolved oxygen in the culture during cultivation, it is possible to control the production ratios of the carotenoid compounds, i.e., β-carotene, echinenone, β-cryptoxanthin, 3-hydroxyechinenone, asteroidenone, canthaxanthin, zeaxanthin, adonirubin, adonixanthin and astaxanthin.

By controlling the concentration of dissolved oxygen in the culture low, it is possible to increase the production ratios of β-carotene, echinenone, canthaxanthin, 3-hydroxyechinenone and adonirubin that are believed to be located upstream in the biosynthesis pathway. By controlling the concentration of dissolved oxygen in the culture at a moderate level, it is possible to increase the production ratio of astaxanthin. By controlling the concentration of dissolved oxygen in the culture high, it is possible to increase the production ratio of adonixanthin.

For example, in order to increase the production ratio of astaxanthin, the concentration of dissolved oxygen in the culture is controlled within a range of 15–40%, preferably 20–30%, of the saturated oxygen concentration. The production ratio of astaxanthin can be increased to 40% or more under conditions that the concentration of dissolved oxygen is 20–30% of the saturated oxygen concentration.

When the concentration of dissolved oxygen is within a range of 0–15%, preferably 0–10%, of the saturated oxygen concentration, β-carotene, echinenone, canthaxanthin, 3-hydroxyechinenone and adonirubin are accumulated abundantly, whereas the production of astaxanthin is inhibited. Under such conditions, the total of the produced β-carotene, echinenone, canthaxanthin, 3-hydroxyechinenone and adonirubin amounts to 60% or more of the total yield of the all compounds. Thus, the production ratio of astaxanthin can be reduced to 40% or less.

In order to increase the production ratio of adonixanthin, the concentration of dissolved oxygen in the culture is controlled within a range of 35–100%, preferably 40–100%, of the saturated oxygen concentration. The production ratio of adonixanthin can be increased to 35% or more under such conditions.

With respect to culture phase, the concentration of dissolved oxygen is important in logarithmic growth phase. For example, when the concentration of dissolved oxygen is raised during this phase, the production ratio of adonixanthin increases even if that concentration is lowered later.

The control of the concentration of dissolved oxygen may be performed by conventional methods used in the culture of microorganisms. For example, the control may be performed by automatically adjusting the flow rate of air or oxygen supplied to the fermenter according to the concentration of dissolved oxygen in the culture which is measured with a dissolved oxygen electrode. Alternatively, the control may be performed by automatically adjusting the rotation speed of an impeller according to the concentration of dissolved oxygen in the culture which is measured with a dissolved oxygen electrode.

EXAMPLES

Hereinbelow, the present invention will be described more specifically with reference to the following Examples. However, the present invention is not limited to these Examples.

Example 1

A medium (100 ml) having the composition as shown in Table 1 below was placed in a 500 ml Erlenmeyer flask and steam-sterilized at 121° C. for 15 min. E-396 strain (FERM BP-4283) was inoculated thereinto and cultured under rotary shaking at 150 rpm and at 28° C. for one day. Subsequently, 600 ml of this culture was inoculated into 20 L of a medium having the composition as shown in Table 2 below contained in a 30 L aeration-agitation fermenter, and cultured under aerobic conditions at an aeration rate of 1.0 vvm and at 28° C. for 90 hr. During cultivation, pH was continuously controlled at 7.2 with 20% NaOH. Since sucrose is consumed as the microorganism grows, 300 g each of sucrose was added on day 1 and day 2 of the cultivation. The dissolved oxygen in the culture was controlled automatically by interlocking a dissolved oxygen electrode with the motor of an impeller and changing the rotation speed of the impeller according to the measured value of the dissolved oxygen. The minimum rotation speed was set at 80 rpm.

The concentration of dissolved oxygen is a ratio to the saturated oxygen concentration in the medium used. In this experiment, the concentrations of dissolved oxygen were set at 5%, 15%, 20%, 25%, 30% and 35% of the saturated oxygen concentration.

The concentrations and ratios of the carotenoid compounds produced under individual conditions were as shown in Tables 4 and 5 below (letters representing these compounds are shown in Table 3).

TABLE 1

| Composition | Amount Added |
|---|---|
| Corn steep liquor | 30 g/L |
| Sucrose | 30 g/L |
| $KH_2PO_4$ | 0.54 g/L |
| $K_2HPO_4$ | 2.78 g/L |
| $MgSO_4.7H_2O$ | 12.0 g/L |
| $CaCl_2.2H_2O$ | 0.1 g/L |
| $FeSO_4.7H_2O$ | 0.3 g/L |
| pH 7.2 | |

TABLE 2

| Composition | Amount Added |
|---|---|
| Corn steep liquor | 30 g/L |
| Sucrose | 30 g/L |
| $KH_2PO_4$ | 1.5 g/L |
| $Na_2HPO_4.12H_2O$ | 3.8 g/L |
| $MgSO_4.7H_2O$ | 3.0 g/L |
| $CaCl_2.2H_2O$ | 0.2 g/L |
| $FeSO_4.7H_2O$ | 1.0 g/L |
| pH 7.2 | |

TABLE 3

| Letter | Compound |
|---|---|
| A | β-carotene |
| B | echinenone |
| C | 3-hydroxyechinenone |
| D | canthaxanthin |
| E | adonirubin |
| F | β-cryptoxanthin |
| G | astaxanthin |
| H | asteroidenone |
| I | adonixanthin |
| J | zeaxanthin |

TABLE 4

| Concentration of Dissolved Oxygen (%) | Concentration of Produced Pigment (mg/L) | | | | | | | | | | |
|---|---|---|---|---|---|---|---|---|---|---|---|
| | A | B | C | D | E | F | G | H | I | J | Total |
| 5 | 5.0 | 1.6 | 0.5 | 3.3 | 4.0 | 0.0 | 2.8 | 0.1 | 0.4 | 0.1 | 17.8 |
| 15 | 2.9 | 2.1 | 0.3 | 3.7 | 7.5 | 0.0 | 8.6 | 0.2 | 1.8 | 0.1 | 27.2 |
| 20 | 3.5 | 2.2 | 0.2 | 2.0 | 3.8 | 0.0 | 11.6 | 0.2 | 3.5 | 0.1 | 27.2 |
| 25 | 3.8 | 1.4 | 0.2 | 1.7 | 4.3 | 0.0 | 14.6 | 0.3 | 5.7 | 0.1 | 32.1 |
| 30 | 2.6 | 0.9 | 0.1 | 0.8 | 1.7 | 0.0 | 9.8 | 0.2 | 5.1 | 0.1 | 21.3 |
| 35 | 1.6 | 0.4 | 0.1 | 0.7 | 1.6 | 0.0 | 8.5 | 0.2 | 7.9 | 0.1 | 21.1 |

TABLE 5

| Concentration of Dissolved Oxygen (%) | Precursors | | G | | I | |
|---|---|---|---|---|---|---|
| | mg/L | % | mg/L | % | mg/L | % |
| 5 | 14.6 | 82 | 2.8 | 16 | 0.4 | 2 |
| 15 | 16.8 | 62 | 8.6 | 32 | 1.8 | 7 |
| 20 | 12.1 | 44 | 11.6 | 43 | 3.5 | 13 |
| 25 | 11.8 | 37 | 14.6 | 46 | 5.7 | 18 |
| 30 | 6.4 | 30 | 9.8 | 46 | 5.1 | 24 |
| 35 | 4.7 | 22 | 8.5 | 40 | 7.9 | 37 |

Precursors: A + B + C + D + E + F

Example 2

A medium (100 ml) having the composition as shown in Table 1 above was placed in a 500 ml Erlenmeyer flask and steam-sterilized at 121° C. for 15 min. E-396 strain (FERM BP-283) was inoculated thereinto and cultured under rotary shaking at 150 rpm and at 28° C. for one day. Subsequently, 100 ml of this culture was inoculated into 2 L of a medium having the composition as shown in Table 2 above contained in a 5 L aeration-agitation fermenter, and cultured under aerobic conditions at an aeration rate of 1.0 vvm and at 28° C. for 90 hr. During cultivation, pH was continuously controlled at 7.2 with 20% NaOH. Since sucrose is consumed as the microorganism grows, 30 g each of sucrose was added on day 1 and day 2 of the cultivation. The dissolved oxygen in the culture was controlled automatically by interlocking a dissolved oxygen electrode with the motor of an impeller and changing the rotation speed of the impeller according to the measured value of the dissolved oxygen. The minimum rotation speed was set at 100 rpm. The concentration of dissolved oxygen is a ratio to the saturated oxygen concentration in the medium used. In this experiment, the concentration of dissolved oxygen was set at 25% of the saturated oxygen concentration.

For the purpose of comparison, the same strain was cultured under conditions that no control of dissolved oxygen was carried out (i.e., agitation was carried out at a constant rotation speed of 450 rpm).

The concentrations of the carotenoid compounds produced under individual conditions were as shown in Table 6.

TABLE 6

| Run No. | Control of Dissolved Oxygen | Precursors | | Astaxanthin | | Adonixanthin | | Total Pigments | |
|---|---|---|---|---|---|---|---|---|---|
| | | mg/L | % | mg/L | % | mg/L | % | mg/L | % |
| 1 | Without (450 rpm) | 16.5 | 62 | 8.6 | 32 | 1.8 | 7 | 26.8 | 100 |
| 2 | Without (450 rpm) | 13.8 | 82 | 2.5 | 15 | 0.5 | 3 | 16.8 | 100 |
| 3 | Without (450 rpm) | 6.5 | 29 | 8.9 | 39 | 5.2 | 23 | 22.6 | 100 |
| 4 | Without (450 rpm) | 10.6 | 45 | 7.1 | 30 | 6.1 | 26 | 23.8 | 100 |
| 5 | Without (450 rpm) | 12.5 | 39 | 14.9 | 47 | 4.6 | 14 | 32.0 | 100 |
| 6 | With (25%) | 11.5 | 38 | 15.3 | 49 | 4.4 | 14 | 31.2 | 100 |
| 7 | With (25%) | 12.8 | 41 | 13.5 | 43 | 4.8 | 15 | 31.1 | 100 |
| 8 | With (25%) | 10.9 | 40 | 11.8 | 43 | 4.5 | 17 | 27.2 | 100 |
| 9 | With (25%) | 13.2 | 44 | 12.5 | 42 | 4.3 | 14 | 30.0 | 100 |
| 10 | With (25%) | 9.9 | 36 | 13.2 | 47 | 4.7 | 17 | 27.8 | 100 |

Example 3

E-396 strain (FERM BP-4283) was mutated with NTG (N-methyl-N'-nitro-N-nitrosoguanidine), and colonies with a deep red color were selected. Carotenoid compounds in culture of these clones were analyzed, followed by selection of a mutant clone Y-071 which had an improved productivity of astaxanthin. A medium (100 ml) having the composition as shown in Table 1 above was placed in a 500 ml Erlenmeyer flask and steam-sterilized at 121° C. for 15 min. Y-1071 clone was inoculated thereinto and cultured under rotary shaking at 150 rpm and at 28° C. for one day.

Subsequently, 100 ml of this culture was inoculated into 2 L of a medium having the composition as shown in Table 2 above contained in a 5 L aeration-agitation fermenter, and cultured under aerobic conditions at an aeration rate of 1.0 vvm and at 28° C. for 90 hr. During cultivation, pH was continuously controlled at 7.2 with 20% NaOH. Since sucrose is consumed as the microorganism grows, 30 g each of sucrose was added on day 1 and day 2 of the cultivation. The dissolved oxygen in the culture was controlled automatically by interlocking a dissolved oxygen electrode with the motor of an impeller and changing the rotation speed of the impeller according to the measured value of the dissolved oxygen. The minimum rotation speed was set at 100 rpm.

The concentration of dissolved oxygen is a ratio to the saturated oxygen concentration in the medium used. In this experiment, the concentrations of dissolved oxygen were set at 5%, 15%, 20%, 25%, 30% and 35% of the saturated oxygen concentration.

The concentrations and ratios of the carotenoid compounds produced under conditions were as shown in Tables 7 and 8 below.

TABLE 7

| Concentration of Dissolved Oxygen (%) | Concentration of Produced Pigment (mg/L) | | | | | | | | | | |
|---|---|---|---|---|---|---|---|---|---|---|---|
| | A | B | C | D | E | F | G | H | I | J | Total |
| 5 | 79.1 | 17.8 | 3.3 | 29.8 | 46.3 | 0.1 | 35.3 | 0.7 | 5.2 | 0.8 | 218.4 |
| 15 | 31.1 | 18.9 | 4.3 | 38.5 | 68.8 | 0.1 | 94.8 | 1.9 | 6.8 | 0.5 | 265.7 |
| 20 | 36.9 | 16.9 | 1.8 | 17.2 | 39.4 | 0.1 | 122.8 | 2.5 | 32.6 | 1.8 | 272.0 |
| 25 | 36.9 | 15.6 | 2.0 | 17.8 | 39.5 | 0.1 | 128.8 | 2.6 | 35.5 | 1.3 | 280.1 |
| 30 | 25.1 | 9.9 | 1.0 | 9.3 | 14.8 | 0.1 | 102.6 | 2.1 | 51.3 | 1.1 | 217.3 |
| 35 | 15.3 | 5.2 | 0.9 | 8.4 | 15.9 | 0.1 | 90.9 | 1.8 | 80.4 | 0.9 | 219.8 |

TABLE 8

| Concentration of Dissolved Oxygen (%) | Precursors | | G | | I | |
|---|---|---|---|---|---|---|
| | mg/L | % | mg/L | % | mg/L | % |
| 5 | 177.9 | 81 | 35.3 | 16 | 5.2 | 2 |
| 15 | 164.1 | 62 | 94.8 | 36 | 6.8 | 3 |
| 20 | 116.6 | 43 | 122.8 | 45 | 32.6 | 12 |
| 25 | 115.8 | 41 | 128.8 | 46 | 35.5 | 13 |
| 30 | 63.4 | 29 | 102.6 | 47 | 51.3 | 24 |
| 35 | 48.5 | 22 | 90.9 | 41 | 80.4 | 37 |

Example 4

A medium (100 ml) having the composition as shown in Table 1 above was placed in a 500 ml Erlenmeyer flask and steam-sterilized at 121° C. for 15 min. A-581–1 strain (FERM BP-671) was inoculated thereinto and cultured under rotary shaking at 150 rpm and at 28° C. for one day. Subsequently, 100 ml of this culture was inoculated into 2 L of a medium the composition as shown in Table 2 above contained in a 5 L aeration-enter, and cultured under aerobic conditions at an aeration rate of 1.0 vvm and at 28° C. for 90 hr. During cultivation, pH was continuously controlled at 7.2 with 20% NaOH. Since sucrose is consumed as the microorganism grows, 30 g each of sucrose was added on day 1 and day 2 of the cultivation. The dissolved oxygen in the culture was controlled automatically by interlocking a dissolved oxygen electrode with the motor of an impeller and changing the rotation speed of the impeller according to the measured value of the dissolved oxygen. The minimum rotation speed was set at 100 rpm. The concentration of dissolved oxygen is a ratio to the saturated oxygen concentration in the medium used. In this experiment, the concentrations of dissolved oxygen were set at 5%, 15%, 20%, 25%, 30% and 35% of the saturated oxygen concentration.

The concentrations and ratios of the carotenoid compounds produced under individual conditions were as shown in Tables 9 and 10 below.

TABLE 9

| Concentration of Dissolved Oxygen (%) | Concentration of Produced Pigment (mg/L) | | | | | | | | | | |
|---|---|---|---|---|---|---|---|---|---|---|---|
| | A | B | C | D | E | F | G | H | I | J | Total |
| 5 | 0.80 | 0.20 | 0.12 | 0.55 | 0.89 | 0.00 | 0.33 | 0.00 | 0.23 | 0.01 | 3.13 |
| 15 | 0.55 | 0.48 | 0.04 | 0.82 | 1.33 | 0.00 | 1.56 | 0.00 | 0.56 | 0.02 | 5.36 |
| 20 | 0.68 | 0.42 | 0.03 | 0.36 | 0.72 | 0.00 | 2.22 | 0.00 | 0.85 | 0.02 | 5.30 |
| 25 | 0.75 | 0.29 | 0.03 | 0.35 | 0.82 | 0.00 | 2.93 | 0.00 | 1.43 | 0.02 | 6.62 |
| 30 | 0.45 | 0.29 | 0.02 | 0.15 | 0.33 | 0.00 | 1.65 | 0.00 | 1.62 | 0.02 | 4.53 |
| 35 | 0.28 | 0.06 | 0.02 | 0.12 | 0.30 | 0.00 | 1.32 | 0.00 | 1.96 | 0.02 | 4.08 |

TABLE 10

| Concentration of Dissolved Oxygen (%) | Precursors | | G | | I | |
|---|---|---|---|---|---|---|
| | mg/L | % | mg/L | % | mg/L | % |
| 5 | 2.6 | 82 | 0.33 | 11 | 0.2 | 7 |
| 15 | 3.2 | 60 | 1.56 | 29 | 0.6 | 10 |
| 20 | 2.2 | 42 | 2.22 | 42 | 0.9 | 16 |
| 25 | 2.3 | 34 | 2.93 | 44 | 1.4 | 22 |
| 30 | 1.3 | 28 | 1.65 | 36 | 1.6 | 36 |
| 35 | 0.8 | 20 | 1.32 | 32 | 2.0 | 48 |

All the publications, patents and patent applications cited in the present specification are incorporated herein by reference in their entireties.

Industrial Applicability

By controlling the concentration of dissolved oxygen in a culture during cultivation, it is possible to change the production ratios of resulting carotenoid compounds in a process of microbiological production of a plurality of carotenoid compounds.

What is claimed is:

1. A process of producing carotenoid compounds by culturing a microorganism producing a plurality of carotenoid compounds, wherein the production ratios of the produced carotenoid compounds are changed by controlling the concentration of dissolved oxygen in the culture during cultivation, and recovering carotenoids from the microorganism, wherein the microorganism is a bacterium in which the nucleotide sequence of its DNA encoding 16S ribosomal RNA has 98% or more homology to the nucleotide sequence of SEQ ID NO: 1.

2. The process according to claim 1, wherein the microorganism is selected from the group consisting of E-396 strain (FERM BP-4283) and mutants thereof, and A-581-1 strain (FERM BP-4671) and mutants thereof.

3. The process according to claim 1, wherein the carotenoid compounds are one or more compounds selected from the group consisting of astaxanthin, adonixanthin, .beta.-carotene, echinenone, canthaxanthin, zeaxanthin, .beta.-cryptoxanthin, 3-hydroxyechinenone, asteroidenone and adonirubin.

4. The process according to claim 1, wherein the production ratio of adonixanthin is increased by controlling the concentration of dissolved oxygen in the culture during cultivation within a range of 40–100% of the saturated oxygen concentration.

5. The process according to claim 1, wherein the production ratio of astaxanthin is increased by controlling the concentration of dissolved oxygen in the culture during cultivation within a range of 20–30% of the saturated oxygen concentration.

6. The process according to claim 1, wherein the concentration of dissolved oxygen in the culture during cultivation is limited to between 0–10% of the saturated oxygen concentration.

7. The process according to claim 1, wherein the microorganism is a bacterium in which the nucleotide sequence of its DNA encoding 16S ribosomal RNA has 99.4% or more homology to the nucleotide sequence SEQ ID NO: 1.

8. A process for producing carotenoid compounds with a decreased proportion of astaxanthin from a genus of bacteria selected from the group consisting of bacterial strains E-396 (FERM BP-4283) and A-581-1 (FERM BP-4671), comprising culturing the bacterium at a restricted oxygen concentration of less than 10% saturated oxygen, and recovering the carotenoid compounds.

* * * * *

SEQUENCE LISTING

<160> NUMBER OF SEQ ID NOS: 2

<210> SEQ ID NO 1
<211> LENGTH: 1452
<212> TYPE: DNA
<213> ORGANISM: Unknown
<220> FEATURE:
<223> OTHER INFORMATION: Nucleotide sequence corresponding to the 16S ribosomal RNA of E-3 96 strain
<221> NAME/KEY: misc_feature
<222> LOCATION: (1350)..(1350)
<223> OTHER INFORMATION: n is A, C, G or T

<400> SEQUENCE: 1

```
agtttgatcc tggctcagaa cgaacgctgg cggcaggctt aacacatgca agtcgagcga    60
gaccttcggg tctagcggcg gacgggtgag taacgcgtgg gaacgtgccc ttctctacgg   120
aatagccccg ggaaactggg agtaataccg tatacgccct ttgggggaaa gatttatcgg   180
agaaggatcg gcccgcgttg gattaggtag ttggtggggt aatggcccac caagccgacg   240
atccatagct ggtttgagag gatgatcagc cacactggga ctgagacacg gcccagactc   300
ctacgggagg cagcagtggg gaatcttaga caatggggga acccctgatc tagccatgcc   360
gcgtgagtga tgaaggcctt agggttgtaa agctctttca gctgggaaga taatgacggt   420
accagcagaa gaagccccgg ctaactccgt gccagcagcc gcggtaatac ggaggggggct   480
agcgttgttc ggaattactg ggcgtaaagc gcacgtaggc ggactggaaa gtcagaggtg   540
aaatcccagg gctcaacctt ggaactgcct ttgaaactat cagtctggag ttcgagagag   600
gtgagtggaa ttccgagtgt agaggtgaaa ttcgtagata ttcggaggaa caccagtggc   660
gaaggcggct cactggctcg atactgacgc tgaggtgcga aagcgtgggg agcaaacagg   720
attagatacc ctggtagtcc acgccgtaaa cgatgaatgc cagacgtcgg caagcatgct   780
tgtcggtgtc acacctaacg gattaagcat tccgcctggg gagtacggtc gcaagattaa   840
aactcaaagg aattgacggg ggcccgcaca agcggtggag catgtggttt aattcgaagc   900
aacgcgcaga accttaccaa cccttgacat ggcaggaccg ctggagagat tcagctttct   960
cgtaagagac ctgcacacag gtgctgcatg gctgtcgtca gctcgtgtcg tgagatgttc  1020
ggttaagtcc ggcaacgagc gcaacccacg tccctagttg ccagcaattc agttgggaac  1080
tctatggaaa ctgccgatga taagtcgag gaaggtgtgg atgacgtcaa gtcctcatgg  1140
gccttacggg ttgggctaca cacgtgctac aatggtggtg acagtgggtt aatccccaaa  1200
agccatctca gttcggattg tcctctgcaa ctcgagggca tgaagttgga atcgctagta  1260
atcgcggaac agcatgccgc ggtgaatacg ttcccgggcc ttgtacacac cgcccgtcac  1320
accatgggag ttggttctac ccgacgacgn tgcgctaacc ttcgggggc aggcggccac  1380
ggtaggatca gcgactgggg tgaagtcgta acaaggtagc cgtagggaa cctgcggctg  1440
gatcacctcc tt                                                      1452
```

<210> SEQ ID NO 2
<211> LENGTH: 1426
<212> TYPE: DNA
<213> ORGANISM: Unknown
<220> FEATURE:
<223> OTHER INFORMATION: Nucleotide sequence corresponding to the 16S ribosomal RNA of A-5 81-1 strain

<400> SEQUENCE: 2

-continued

```
tagagtttga tcctggctca gaacgaacgc tggcggcagg cttaacacat gcaagtcgag      60
cgagaccttc gggtctagcg gcggacgggt gagtaacgcg tgggaacgtg cccttctcta     120
cggaatagcc ccgggaaact gggagtaata ccgtatacgc cctttggggg aaagatttat     180
cggagaagga tcggccgcg ttggattagg tagttggtga ggtaacggct caccaagccg      240
acgatccata gctggtttga gaggatgatc agccacactg ggactgagac acggcccaga    300
ctcctacggg aggcagcagt ggggaatctt agacaatggg ggcaaccctg atctagccat    360
gccgcgtgag tgatgaaggc cttaggggttg taaagctctt tcagctggga agataatgac   420
ggtaccagca gaagaagccc cggctaactc cgtgccagca gccgcggtaa tacggagggg   480
gctagcgttg ttcggaatta ctgggcgtaa agcgcacgta ggcggactgg aaagtcagag    540
gtgaaatccc agggctcaac cttggaactg cctttgaaac tatcagtctg gagttcgaga   600
gaggtgagtg gaattccgag tgtagaggtg aaattcgtag atattcggag gaacaccagt    660
ggcgaaggcg gctcactggc tcgatactga cgctgaggtg cgaaagcgtg gggagcaaac   720
aggattagat accctggtag tccacgccgt aaacgatgaa tgccagacgt cggcaagcat    780
gcttgtcggt gtcacaccta acggattaag cattccgcct ggggagtacg gtcgcaagat   840
taaaactcaa aggaattgac gggggcccgc acaagcggtg gagcatgtgg tttaattcga    900
agcaacgcgc agaaccttac caaccctgga catggcagga ccgctggaga gattcagctt   960
tctcgtaaga gacctgcaca caggtgctgc atggctgtcg tcagctcgtg tcgtgagatg   1020
ttcggttaag tccggcaacg agcgcaaccc acgtccctag ttgccagcat tcagttgggc  1080
actctatgga aactgccggt gataagccgg aggaaggtgt ggatgacgtc aagtcctcat  1140
ggcccttacg ggtgggcta cacacgtgct acaatggtgg tgacagtggg ttaatcccca   1200
aaagccatct cagttcggat tgtcctctgc aactcgaggg catgaagttg gaatcgctag  1260
taatcgcgga acagcatgcc gcggtgaata cgttcccggg ccttgtacac accgcccgtc  1320
acaccatggg agttggttct acccgacgac gctgcgctaa cccttcgggg aggcaggcgg  1380
ccacggtagg atcagcgact ggggtgaagt cgtaacaagg tagcca                  1426
```